US007404639B2

(12) United States Patent
Nishihira et al.

(10) Patent No.: US 7,404,639 B2
(45) Date of Patent: Jul. 29, 2008

(54) APPARATUS FOR RECOVERING EYESIGHT UTILIZING STEREOSCOPIC VIDEO AND METHOD FOR DISPLAYING STEREOSCOPIC VIDEO

(75) Inventors: Takashi Nishihira, Tokyo (JP); Hirofumi Tahara, Tokyo (JP)

(73) Assignee: Olympus Visual Communications Corp., Tokyo (JP)

( * ) Notice: Subject to any disclaimer, the term of this patent is extended or adjusted under 35 U.S.C. 154(b) by 600 days.

(21) Appl. No.: 10/477,260

(22) PCT Filed: Dec. 10, 2001

(86) PCT No.: PCT/JP01/10799

§ 371 (c)(1), (2), (4) Date: Jun. 10, 2004

(87) PCT Pub. No.: WO02/091983

PCT Pub. Date: Nov. 21, 2002

(65) Prior Publication Data

US 2004/0207810 A1 Oct. 21, 2004

(30) Foreign Application Priority Data

May 11, 2001 (JP) ............................ 2001-179352

(51) Int. Cl.
*A61B 3/00* (2006.01)
*A61B 3/10* (2006.01)
*A61B 3/14* (2006.01)

(52) U.S. Cl. ....................... 351/203; 351/200; 351/204; 351/206

(58) Field of Classification Search ................. 351/203, 351/200, 204, 211, 221
See application file for complete search history.

(56) References Cited

FOREIGN PATENT DOCUMENTS

| | | | |
|---|---|---|---|
| JP | 58-117535 | | 7/1983 |
| JP | 08-257078 | * | 3/1995 |
| JP | 8-257078 | | 10/1996 |
| JP | 9-166955 | | 6/1997 |
| JP | 2002-120125 | | 4/2002 |

* cited by examiner

*Primary Examiner*—Ricky Mack
*Assistant Examiner*—Brandi N Thomas
(74) *Attorney, Agent, or Firm*—Brooks Kushman P.C.

(57) ABSTRACT

This invention provides a stereo image displaying method and eyesight recovery apparatus which stimulates the eye muscles and is inexpensive and simple.

An image for the left and the right eye are displayed on the screen 50 of an electronic device 2 alternately, an observer wears spectacles 4 which open and close in synchronism with the display of these images to produce a convergence angle and parallax to obtain a 3-D image. A 3-D image display device is used to enable the observer to focus his/her right and left eyes on the images of a 3-D image. A 3-D image 10*a* is displayed at a position close to the spectacles 4 and then gradually moved away from it. The eyesight recovery apparatus comprises a movement control unit 10 for moving a 3-D image 10*b* at a distance close to the spectacles 4 and a repetition control unit 23 for repeating the receding and approach movements. When the observer wearing the spectacles 4 tries to always focus on the 3-D images 10*a* and 10*b* on the screen 50, his/her ciliary bodies and eyeball moving muscles around his/her eyes are stimulated, thereby recovering his/her eyesight.

12 Claims, 3 Drawing Sheets

APPARATUS FOR RECOVERING EYESIGHT UTILIZING STEREOSCOPIC VIDEO AND METHOD FOR DISPLAYING STEREOSCOPIC VIDEO

FIELD OF THE INVENTION

The present invention relates to a stereo image displaying method and eyesight recovery apparatus which stimulate the eye muscles of an observer when he/she looks at a three-dimensional (3-D) perspective image displayed on a VDT electronic display device through spectacles with shutters or without spectacles.

BACKGROUND OF THE INVENTION

Due to the spread of personal computers, the popularization of TV games, the use of portable telephones as a necessity of life and the continuous appreciation of TV programs in recent years, people look at the screen of a VDT (Visual Display Terminal) from a distance of less than 1 m very frequently. Therefore, the population of personal computer type short-sighted people is sharply increasing. To cure this personal computer type short-sightedness, an MD-SS eyesight recovery and training apparatus which has been developed by an ophthalmologist is used As shown in FIG. 6, in the eyesight recovery and training apparatus 30, a groove 33 is formed in a long table mounted on a base 31 horizontally and a target body 34 is set in such a manner that it can move along this groove 33. The target body 34 consists of a flat plate 35 and a strut 36, and a Randolt ring is drawn on the white flat plate 35. The Randolt ring is a mark used for a general eye test, and a upper, lower, left or right part of the ring is cut away. The strut 36 is moved along the groove 33 in a horizontal direction by a predetermined drive unit together with the flat plate 35, and a trainee sits opposite to the flat plate 35 with his/her chin applied to a square frame 39 before him/her.

The flat plate 35 can approach up to 10 cm before the eyes of the trainee within the square frame 39 and can recede up to 2 m from the eyes. In the training method, for a short-sighted trainee, the flat plate 35 is first moved from 10 cm before the eyes of the trainee within the square frame 39 and moved faster in the receding direction, for example, up to 2 m in 3 seconds.

When the flat plate 35 is to be returned from 2 m away from the trainee within the square frame 39, the moving speed of the flat plate 35 is slowed down in the approaching direction, for example, up to 10 cm before the eyes in 12 seconds. For a far-sighted trainee, the flat plate 35 is moved at reverse speeds. This training is carried out for three minutes each time. By chasing the flat plate 35 with the both eyes of the trainee, the ciliary bodies and eyeball moving muscles of the trainee are trained to form an image of the outside world on the retinae of the eyes.

For a direction and distance training method, a 15-point sheet 40 shown in FIG. 7 is used. On the 15-point sheet 40, there are shown numerals 1 to 5 at an upper position from left to right at equal intervals, numerals 6 to 10 at the middle from left to right at equal intervals and numerals 11 to 15 at a lower position from left to right at equal intervals. The trainee holds the 15-point sheet with his/her both hands and tries to see numerals 1 to 15 sequentially by moving his/her eyeballs while turning his/her face toward the numeral 8. Then, he/she tries to see numerals 1 and 2 at the same time and up to numerals 13 and 14 sequentially by moving his/her eyeballs.

Thereafter, he/she tries to see numerals 1, 2 and 3 at the same time and up to 13, 14 and 15 sequentially by moving his/her eyeballs. Further, he/she tries to see numerals 1, 2, 3 and 4 at the same time and up to numerals 13, 14 and 15 sequentially by moving his/her eyeballs. The number of numerals to be seen at the same time is increased, or the order of numerals to be seen is reversed. This test is repeated for 10 minutes or more each day. Thus, the ciliary bodies and eyeball moving muscles are trained.

Although the conventional MD-SS eyesight recovery and training apparatus is very effective in the recovery of eyesight, a trainee must go to a clinic. Therefore, a trainee who is busy cannot benefit from the apparatus. Although the apparatus can be purchased, it is expensive and 2 m or more long, a large space in a house is required to install it. Although an apparatus employing a direction and distance training method is simple, inexpensive, effective and handy, the number of trainees who continue training with the apparatus is decreasing due to laziness.

It is an object of the present invention to provide to a stereo image displaying method and eyesight recovery apparatus which stimulate the eye muscles and which enable a trainee who is busy and wishes to recover his/her eyesight and even a trainee who is lazy in eyesight recovery training to continue training without fail and which are simple in structure, inexpensive and effective.

SUMMARY OF THE INVENTION

The present invention has been made to solve the above problem.

According to a first aspect of the present invention, there is provided an to a stereo image displaying method comprising the steps of:

displaying a 3-D image at a position close to spectacles using a 3-D image display device which displays an image for the left eye and an image for the right eye on an electronic display screen alternatively, allows an observer wearing spectacles which open and close in synchronism with the display of these images to see the images to produce a convergence angle and parallax so as to obtain the 3-D image and makes his/her right and left eyes focus on the images in order to recognize the 3-D image;

gradually moving the 3-D image away from the spectacles;

moving the 3-D image at a distance close to the spectacles in the opposite direction; and repeating the receding/approaching movements.

According to a second aspect of the present invention, in eyesight recovery apparatus which displays an image for the left eye and an image for the right eye on an electronic display screen alternatively, allows an observer wearing spectacles which open and close in synchronism with the display of these images to see the images to produce a convergence angle and parallax so as to obtain the 3-D image and makes his/her right and left eyes focus on the images in order to recognize the 3-D image, there is provided an eyesight recovery apparatus which comprises a movement control unit for displaying the 3-D image at a position close to the spectacles, gradually moving the 3-D image away from the spectacles, and moving the 3-D image at a distance close to the spectacles in the opposite direction; and a repetition control unit for repeating the receding/approaching movements to stimulate the ciliary bodies and eyeball moving muscles of the observer when he/she always tries to focus on this 3-D image.

According to a third aspect of the present invention, in eyesight recoverry program which displays an image for the left eye and an image for the right eye on an electronic display screen alternatively, allows an observer wearing spectacles which open and close in synchronism with the display of these images to see the images to produce a convergence angle and parallax so as to obtain the 3-D image and makes his/her right and left eyes focus on the images in order to recognize the 3-D image, there is provided an eyesight recovery apparatus which comprises a movement control unit for displaying the 3-D image at a position close to the spectacles, gradually moving the 3-D image away from the spectacles, and moving the 3-D image at a distance close to the spectacles in the opposite direction; and a repetition control unit for repeating the receding/approaching movements to stimulate the ciliary bodies and eyeball moving muscles of the observer when he/she always tries to focus on this 3-D image.

DETAILED DESCRIPTION

An image of an object is formed on human right and left eyes with a parallax that even the same object is shifted in a horizontal direction. The parallax of an object close to the eyes is larger than the parallax of an object far away from the eyes. As the object is farther away from the eyes, the parallax becomes smaller. Further, although the right and left eyes form a convergence angle for an object to be seen, the convergence angle of an object close to the eyes is larger than the convergence angle of an object far away from the eyes. The convergence angle becomes smaller as the object is farther away from the eyes. The human brain forms a three-dimensional (3-D) image of an object from its convergence angle and parallax and judges the distance of the object.

Meanwhile, a 3-D namely stereo image display device produces a convergence angle and parallax in a displayed image electronically. When a specific 3-D image is to be seen, the ciliary bodies and eyeball moving muscles of the right and left eyes become active to focus on the image (virtual image). According to the experiments of the inventor of the present invention, a trainee felt tired around his/her eyes as much as he/she received training with the MD-SS eyesight recovery and training apparatus and direction/distance training method.

Figure 1:
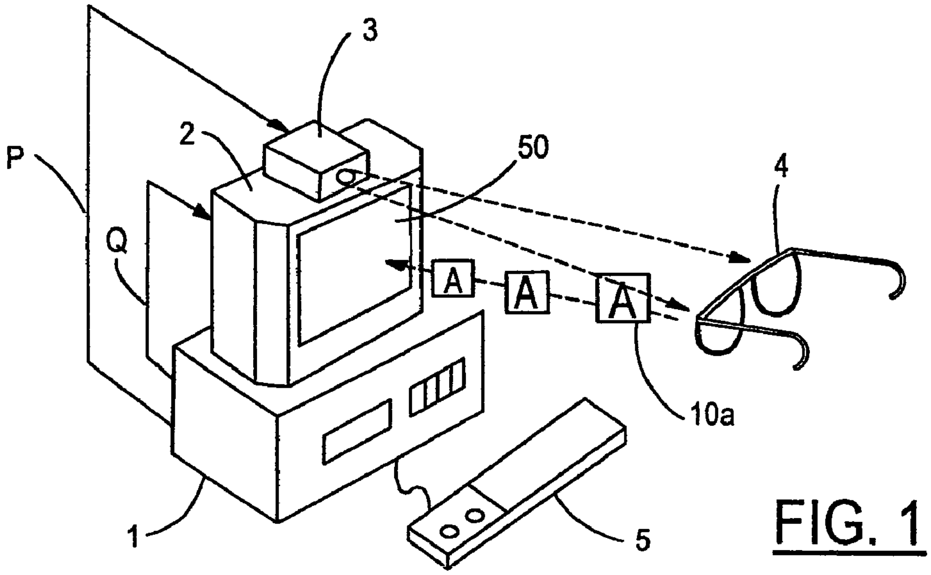
FIG. 1 is a diagram showing the whole appearance of the eyesight recovery apparatus of the present invention.

As for the eyesight recovery method and apparatus of the present invention, a case where the eyesight recovery apparatus used is a desk-top personal computer will be described hereinbelow. FIG. 1 shows the whole appearance of the eyesight recovery apparatus. In FIG. 1, this eyesight recovery apparatus comprises a 3-D image display device, logic circuit 1, display unit 2, infrared light emitting unit 3, spectacles with shutters 4 and keyboard 5. Since the spectacles with shutters 4 which are used to see a 3-D image and the infrared light emitting unit 3 are already described in detail in U.S. Pat. No. 5,808,588, so their descriptions are omitted.

The logic circuit 1 is a main body and comprises a reading unit such as CD-ROM (disk-type high-density reading and recording medium), FD (floppy disk) or DVD and a hard disk as a memory. The CD-ROM, FD or HD stores an eyesight recovery program (software) together with other programs. The eyesight recovery program shows an image similar to the flat plate 35 used in the conventional MD-SS eyesight recovery and training apparatus or a 3-D image similar to the numerals shown in the 15-point sheet used in the direction/distance training method.

Figure 2:
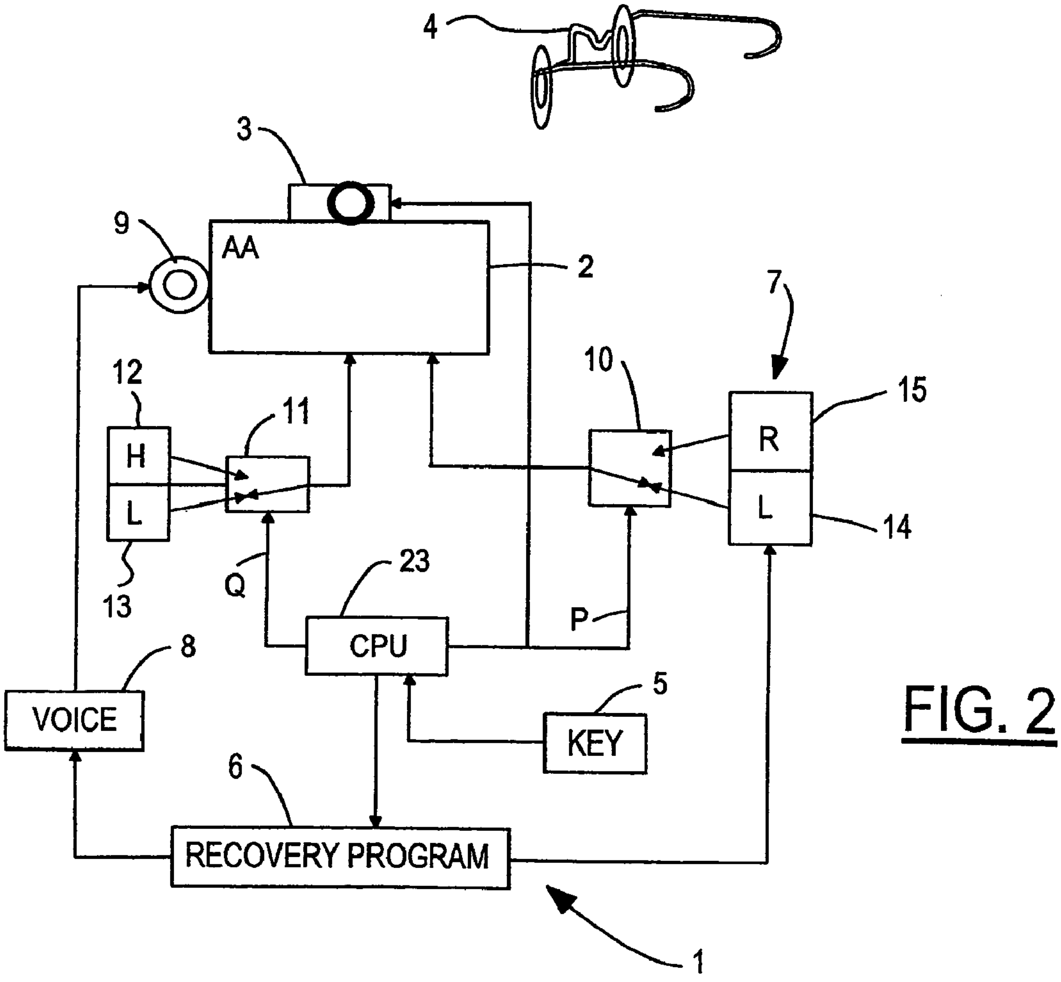
FIG. 2 is a circuit diagram of the eyesight recovery apparatus of the present invention.

The circuit configuration of the eyesight recovery apparatus will be detailed with reference to FIG. 2. In FIG. 2, the eyesight recovery apparatus comprises a display unit 2, speaker 9, spectacles 4, keyboard 5, infrared light emitting unit 3 and logic circuit 1. The logic circuit 1 comprises a CPU 23, basic memory 6, image memory 7, sound memory 8, first electronic switch 10, second electronic switch 11, first mode generating unit 12, second mode generating unit 13 and infrared light emitting unit 3.

The base memory 6 stores software which is input from CD-ROM or FD. This software is separated according to an instruction from the CPU 23 to send 3-D image data to the 3-D image memory 7 and sound data to the sound memory 8. The image memory 7 consists of a left memory 14 and a right memory 15, and the first electronic switch 10 switches between the left memory 14 and the right memory 15 according to a timing signal P from the CPU 23 to read image data. This timing signal P is also sent to the infrared light emitting unit 3.

The second electronic switch 11 switches between the first mode generating unit 12 and the second mode generating unit 13 according to a switch signal Q from the CPU 23. The first mode generating unit 12 has a normal display speed of 60 cycles and the second mode generating unit 13 has a high display speed of 120 cycles.

The CPU 23 switches the display unit 2 from a normal scan mode to a double scan mode (high speed). As the structure of a 3-D image TV is disclosed in detail by JP-A 8-20551, JP-A 9-200804 and U.S. Pat. No. 5,510,832, so its description is omitted. A personal computer has a screen of a non-interlace type high-resolution ordinary scan mode whereas an expensive digital display has a large-sized screen of a non-interlace type high resolution and high-speed scan mode in automatic response to the characteristics of an input video signal, and the mode is switched by the electronic switch 11 based on an instruction from the CPU 23.

Thus, an image for the left eye and an image for the right eye are displayed alternately on the screen 50 of the 3-D image display device. The spectacles 4 with shutters are provided with liquid crystal shutters corresponding to the right and left liquid crystal lenses, and the shutters are opened or closed in accordance with an infrared opening/closing signal from the infrared light emitting unit 3. In the brain, images from the right and left eyes are compounded to recognize a 3-D image on the display unit 50. Since the left and right eyes see 30 Hz images, respectively, a smooth 3-D image can be recognized naturally.

The spectacles 4 are not always required but the spectacles 4 in use help for the right and left eyes to recognize the right and left eyes image respectively on the display unit 50.

A description is subsequently given of the operation of the apparatus. When an operator of office equipment or game player sits in front of a personal computer and starts to use the personal computer, the eyesight recovery program is read from the CD-ROM, FDD, HD or the base memory 6 by the CPU 23. The player becomes an observer or trainee automatically. When the menu includes a 3-D perspective image and 3-D directional image and a 3-D perspective image is selected, an image shown in FIG. 3 is displayed (conceptually) or when a 3-D directional image is selected, an image shown in FIG. 4 is displayed on the display unit 2 (conceptually).

Figure 3:
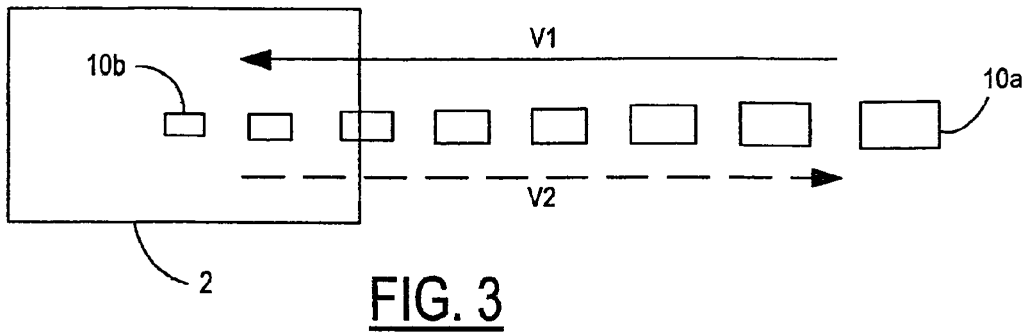
FIG. 3 is a diagram for explaining a case where a 3-D perspective image is used in the eyesight recovery method of the present invention.
Figure 4:
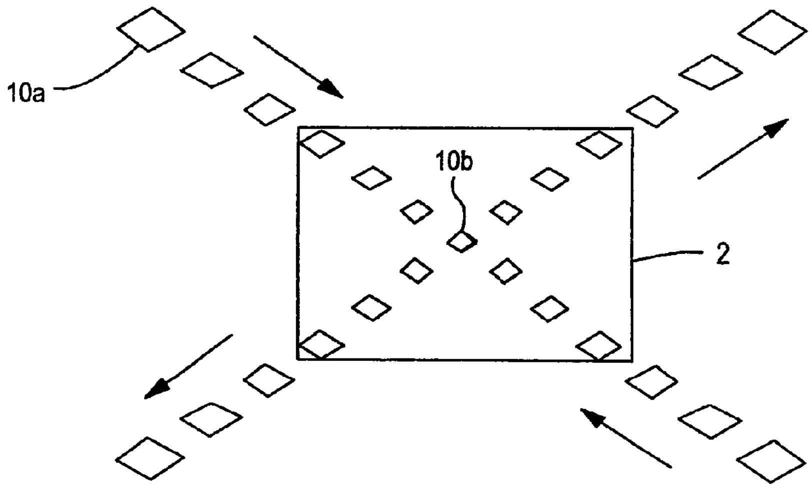
FIG. 4 is a diagram for explaining that the eyesight recovery method of the present invention is a direction/distance training method.

In the case of a 3-D perspective image, in FIG. 3, a 3-D image 10*a* is displayed at a position close to the spectacles 4 on the display unit 2 (the image is displayed on the display unit 2) and then displayed as if it gradually went away from the spectacles 4. After the passage of a predetermined time, a 3-D image 10*b* is displayed. The trainee wearing the spectacles 4 adjusts his/her focusing point so that he/she can see the 3-D image 10*b* clearly.

When the 3-D image 10*a* is a character, the trainee tries to read the character, whereby his/her ciliary bodies and eyeball moving muscles become active automatically to adjust the thickness of his/her crystalline lenses so that an image of the character is focused on his/her retinas accurately. To read the character, the ciliary bodies and eyeball moving muscles become active to focus the 3-D image on the retina. In the case of a 3-D perspective image, the trainee can input the receding speed v1, the moving distance L and the specification of sound during training. For example, the trainee can input a moving distance L of 10 m, a receding speed v1 of 10 m/6 seconds and an approaching speed v2 of 10 m/12 seconds from the keyboard 5.

Figure 5:
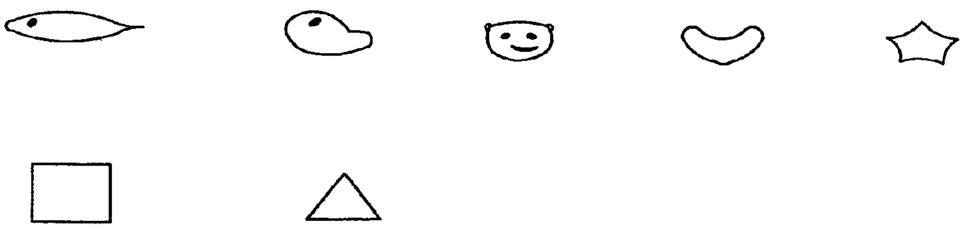
FIG. 5 is a diagram showing the type of a 3-D image of the eyesight recovery apparatus of the present invention.
Figure 6:
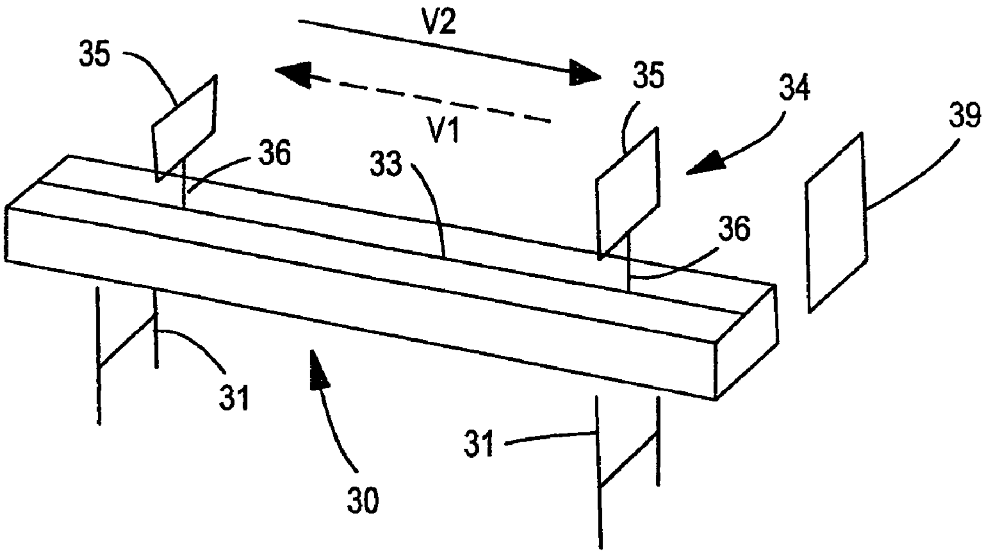
( Prior Art ) FIG. 6
FIG. 6 is a diagram for explaining that the conventional eyesight recovery method is a perspective method using an actual object.
Figure 7:
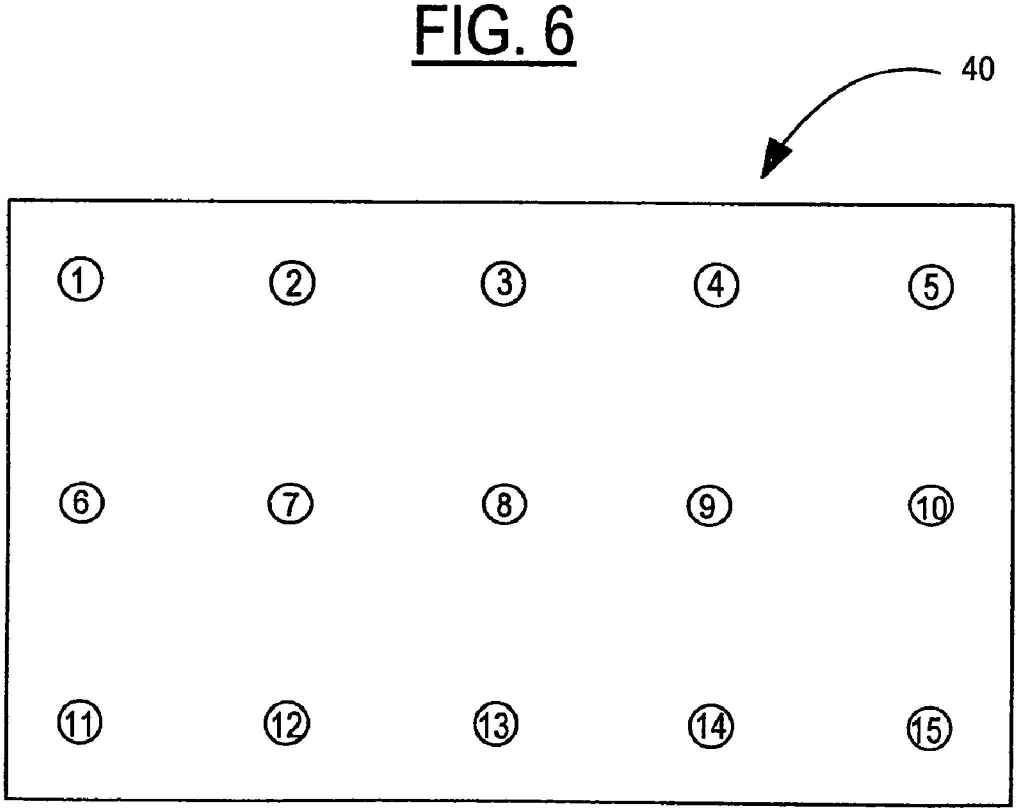
( Prior Art ) FIG. 7
FIG. 7 is a diagram for explaining the conventional direction/distance training method using an actual object.

As for other forms of the 3-D image 10*a*, as shown in FIG. 5, an animal like a fish, cat, heart, star, circle, triangle, square or other 3-D character can be selected. The size of the 3-D image 10*a* can be set freely and its color can also be selected from red, blue, yellow, purple, orange, pink or color striped pattern. Sound data from the sound memory 8 is sent to the speaker 9 after predetermined processing sound during training can be selected from the recitation of a poem composed by Tohson Shimazaki, classical music, Japanese popular song, Western popular song, jazz, folk song, wind sound, wave sound and the like.

By setting the number of seconds for dividing the moving distance L of the 3-D image to a large or small value, the receding speed of the 3-D image is adjusted. Since a young short-sighted trainee has the difficulty of seeing an object at a distance, the receding speed v1 is set high (the number of seconds is set to a small value) in FIG. 3 in order to improve the momenta of the ciliary body and the eyeball moving muscle. Since a young short-sighted trainee can see an object close at hand, the approaching speed v2 is set low (the number of seconds is set to a large value) in order to moderate the momenta of the ciliary body and the eyeball moving muscle.

Since an aged far-sighted trainee can see an object at a distance well, the receding speed v1 is set low (the number of seconds is set to a large value) in order to moderate the momenta of the ciliary body and the eyeball moving muscle. Since an aged far-sighted trainee has the difficulty of seeing an object close at hand, the approaching speed v2 is set high (the number of seconds is set to a small value) in order to improve the momenta of the ciliary body and the eyeball moving muscle. Before starting office work with a personal computer or during a recess or after the end of the recess, this training is carried out for about 3 or 4 minutes. In a method similar to this direction/distance training method, as shown in FIG. 4, the 3-D image 10*a* approaches very close to an upper left position of the left eye and then recedes toward the deep center of the screen.

The receding speed and approaching speed of the 3-D image can be set to appropriate values from the keyboard 5. The trainee tries to chase this 3-D image 10*a* with his/her both eyes. The trainee tries to see (focus on) a character, for example, as the 3-D image 10*a* by moving his/her both eyeballs while he/she turns his/her face forward. By chasing the 3-D image with his/her both eyes, the ciliary bodies and eyeball moving muscles of his/her both eyes move actively or try to move actively (expand or shrink).

Thereafter, the 3-D image 10*b* approaches toward the upper right direction of the right eye gradually from the deep center of the screen. Although the actual 3-D image is displayed on the screen, as the both eyes of the trainee must focus on its virtual image to see the 3-D image, the ciliary bodies and eyeball moving muscles of the both eyes must move as when the actual object recedes or approaches. Further, the 3-D image approaches very close to the upper right direction of the right eye and gradually recedes toward the deep center of the screen.

Then, the 3-D image 10*b* approaches toward the lower right direction of the right eye from the deep center of the screen. Similarly, the 3-D image approaches very close to the lower left direction of the left eye and gradually recedes toward the deep center of the screen. The approaching and receding positions, speeds and moving orders can be suitably set from the keyboard 5 according to the eyesight of the trainee.

Even with this method, the size of the 3-D image 10*a* can be freely set from the keyboard 5, and the color of the 3-D image can be selected from red, blue, yellow, purple, orange, pink and color striped pattern. The sound during training can be selected from, for example, the recitation of a poem composed by Tohson Shimazaki, classic music, Japanese popular song, Western popular song, jazz, folk song, wind sound and wave sound.

Before the start of office work with a personal computer or during or at the end of a recess, the CPU 23 always reads this eyesight recovery software from the base memory 6 and executes this software. This training must be carried out for about 3 or 4 minutes by setting the minimum time with a timer or the like each time he/she sits in front of a personal computer.

The electronic display device 2 may be a desk-top electronic computer (CRT type personal computer), notebook type electronic computer (liquid crystal type small-sized personal computer), portable telephone (PHS or other telephone with a liquid crystal display), portable electronic terminal (PDA), helmet type electronic display device (HMD), electronic display device with built-in spectacles, or TV game device (TV receiver used as a display device) if it has a 3-D image display function. Further, the 3-D image display device may be a reticular type, parallax barrier type or double-image splitter type 3-D image display device which does not need spectacles. The trainee tries to read the 3-D image 10*a*, whereby his/her ciliary bodies and eyeball moving muscles become active automatically, various muscles around eyeball are stimulated.

The device for stimulating the ciliary bodies and eyeball moving muscles gives eyesight recovery performance.

Since the eyesight recovery apparatus can be used by anyone at any time and anywhere, for example, at an office, home or commuter train as described above, a person who is very busy and wishes to recover his/her eyesight and a person who is lazy in training for the recovery of his/her eyesight can continue training without fail. Since the apparatus of the present invention simply incorporates a program or software and has a 3-D image display function, his/her personal computer can be used as the apparatus. Therefore, the apparatus is inexpensive and can be expected to achieve a great effect. Looking at an electronic display device is now part of routine work and therefore it is apprehended that the population of short-sighted people and people with eyestrain and astigmatism is growing. In contrast to this, when these electronic devices are provided with a 3-D image display function and the eyesight recovery method and apparatus of the present invention are applied to these devices, the recovery of eyesight can be carried out during working hours automatically and forcedly.

What is claimed is:

1. An eyesight recovery method comprising the steps of:

reading out 3-D image data comprising perspective image data for left and right eyes from a memory;

separating the 3-D image data into image data for the left eye and image data for the right eye;

storing the image data for the left eye and the image data for the right eye in an image memory;

sending a timing signal to the image memory and to an infrared light emitting unit;

alternately reading out the image data for the left eye and the image data for the right eye from the image memory according to the timing signal;

emitting infrared light from the infrared light emitting unit to spectacles according to the timing signal;

opening and closing the shutters of the spectacles in accordance with the infrared light from the infrared light emitting unit;

displaying a 3-D image based on the image data for the left eye and the image data for the right eye using a 3-D image display device which displays an image for the left eye and an image for the right eye on a single electronic display screen alternately and synchronously according to the timing signal, wherein the electronic display screen is remotely separated and detached from the spectacles and remains located at a stationary position;

allowing an observer wearing the spectacles in which the shutters of the spectacles open and close in synchronism with respect to the display of the images on the electronic display screen to see the images to produce a convergence angle and parallax so as to obtain the 3-D image and make the observer's right and left eyes focus on the images in order to recognize the 3-D image;

displaying the 3-D image on the electronic display screen for the observer to see at a position close to the spectacles;

displaying a receding movement of the 3-D image on the electronic display screen for the observer to see the 3-D image gradually moving away from the spectacles;

displaying an approaching movement of the 3-D image on the electronic display screen at a distance from the spectacles for the observer to see the 3-D image gradually moving toward the spectacles; and repeating the displayed receding/approaching movements of the 3-D image on the electronic display screen to stimulate the ciliary bodies and eyeball moving muscles of the observer in order to recover the observer's eyesight as a result of the observer continuously focusing on the images displayed on the electronic display screen in order to see the 3-D image.

2. The eyesight recovery method according to claim 1, wherein sound based on sound data read out from the memory with the 3-D image data is reproduced on a speaker during the receding and approaching movements.

3. The eyesight recovery method according to claim 1, wherein the approaching speed of the 3-D image differs from the receding speed of the 3-D image.

4. The eyesight recovery method according to claim 1, wherein the receding and approaching movements of the 3-D image are carried out between the front of the spectacles and the center portion of the screen.

5. The eyesight recovery method according to claim 1, wherein the receding and approaching movements of the 3-D image are carried out between the upper left or upper right portion of the spectacles and the center portion of the screen.

6. The eyesight recovery method according to claim 1, wherein the receding and approaching movements of the 3-D image are carried out between the lower left or lower right portion of the spectacles and the center portion of the screen.

7. The eyesight recovery method according to claim 1, wherein the receding and approaching speeds of the 3-D image differ from each other and are set according to the eyesight of the observer.

8. The eyesight recovery method according to claim 1, wherein the number of repetitions of the receding and approaching movements of the 3-D image is set according to the eyesight of the observer.

9. The eyesight recovery method according to claim 1, wherein the 3-D image is supplied to the 3-D image display device as a program from the memory.

10. The eyesight recovery method according to claim 1, wherein the 3-D image is a character, symbol, or pattern.

11. The eyesight recovery method according to claim 1, wherein a character, symbol, or pattern is displayed 3-dimensionally as the 3-D image with shade.

12. The eyesight recovery method according to claim 11, wherein the 3-D image is turned during its receding and approaching movements.

* * * * *